(12) United States Patent
Kassies et al.

(10) Patent No.: US 8,962,931 B2
(45) Date of Patent: Feb. 24, 2015

(54) **CVYV-RESISTANT PLANTS OF THE SPECIES *CUCUMIS MELO***

(75) Inventors: Wietsche Kassies, Enkhuizen (NL); Teresa Maria Montoro Ponsoda, Aguadulee (ES); Nanne Machiel Faber, Hoorn (NL); Jacob Pieter Mazereeuw, Enkhuizen (NL); Ana Belen Zapata Barrera, Roquetas de Mar (ES)

(73) Assignee: Enza Zaden Beheer B.V., Enkhuizen (NL)

( * ) Notice: Subject to any disclaimer, the term of this patent is extended or adjusted under 35 U.S.C. 154(b) by 983 days.

(21) Appl. No.: 13/056,631

(22) PCT Filed: Sep. 2, 2008

(86) PCT No.: PCT/EP2008/007214
§ 371 (c)(1),
(2), (4) Date: Apr. 22, 2011

(87) PCT Pub. No.: WO2010/025747
PCT Pub. Date: Mar. 11, 2010

(65) Prior Publication Data
US 2011/0214202 A1    Sep. 1, 2011

(51) Int. Cl.
*A01H 1/02* (2006.01)
*A01H 1/04* (2006.01)
*A01H 5/08* (2006.01)

(52) U.S. Cl.
CPC ........................................ *A01H 5/08* (2013.01)
USPC ........... 800/309; 800/266; 800/265; 800/267; 800/307; 435/6.11

(58) Field of Classification Search
CPC ............. A01H 5/08; A01H 1/04; A01H 5/00; C12N 15/8216; C12N 15/8257; C12N 15/8203; C12N 15/8283; C12N 15/8213; C12N 15/8217; C12N 15/8218; C12N 15/8239; C12N 15/8242; C12N 15/8247; C12N 2770/40022
See application file for complete search history.

(56) References Cited

PUBLICATIONS

Marco, C.F., et al., "Evaluation of several accessions and wild relatives of *Cucumis melo* against cucumber vein yellowing virus (CVYV)" Cucurbi Genetics Cooperative Report, vol. 26, (2003) pp. 7-8.

*Primary Examiner* — Brent T Page
*Assistant Examiner* — Jared Shapiro
(74) *Attorney, Agent, or Firm* — The Webb Law Firm

(57) ABSTRACT

The present invention relates to *Cucumis melo* plants that are resistant against Cucumber Vein Yellowing Virus (CVYV), and to plant parts derived thereof without the occurrence of necrotic symptoms. The invention further relates to methods of producing said plants, to CVYV-resistant plants obtainable by said methods, as well as to plant parts derived from said CVYV-resistant plants. Specifically, the present invention relates to a plant of the species *Cucumis melo*, comprising in its genome a genetic element, said genetic element comprising a Cucumber Vein Yellowing Virus (CVYV)-resistance conferring Quantitative Trait Locus (QTL), or a CVYV-resistance conferring part thereof, genetically linked to at least one molecular marker, wherein said marker is selected from a group consisting of E13/M48-259.69-P2, E16/M48-377.36-P2, E13/M48-261.30-P2 and E26/M62-076.8-P2.

8 Claims, No Drawings

US 8,962,931 B2

CVYV-RESISTANT PLANTS OF THE SPECIES *CUCUMIS MELO*

The present invention relates to *Cucumis melo* plants that are resistant against Cucumber Vein Yellowing Virus (CVYV), and to plant parts derived thereof. The invention further relates to methods of producing said plants, to CVYV-resistant plants obtainable by said methods, as well as to plant parts derived from said CVYV-resistant plants.

CVYV belongs to the genus Ipomovirus of the family Potyviridae. It is a rather unstable virus with rod-shaped particles, generally being 740-800 nm long and 15-18 nm wide. The viral nucleic acid of CVYV has been reported to consist of double stranded RNA.

The virus has a narrow host range that is mainly restricted to plants of the family of Cucurbitaceae. This family includes economic important crops like cucumbers, squashes (including pumpkins), melons and watermelons. Although CVYV infections generally are a problem in cucumber production, also squash, zucchini, watermelon and melon productions are affected.

CVYV is generally transmitted by the whitefly *Bremisia tabaci*. CVYV infected plants of the species *Cucumis melo* (melon) show vein yellowing or vein clearing and stunting with corresponding yield reduction. CVYV infection may also cause death of the plants.

Thus, CVYV can have disastrous effects in crops when they become contaminated. Prevention of infection, by, for example, raising seedlings in a whitefly free environment, or treatment using for example pesticides, generally is costly and/or unfriendly to the environment. In addition, these methods do not always provide satisfactory results.

No resistance to CVYV has been described in plants of the species *Cucumis melo* so far, although several attempts to find such resistance have been undertaken. Resistance to CVYV has been reported for other *Cucumis* species like *C. africanus*, *C. dipsaceus*, and *C. prophetarum* (Nieto et al. BMC Plant Biology (2007) 7: 34). The object of the present invention is to provide plants of the species *Cucumis melo* that are resistant to CVYV.

This object is achieved by the invention by providing a plant of the species *Cucumis melo*, comprising in its genome a genetic element, said genetic element comprising a Cucumber Vein Yellowing Virus (CVYV)-resistance conferring Quantitative Trait Locus (QTL), or a CVYV-resistance conferring part thereof, genetically linked to at least one molecular marker, wherein said marker is selected from to the group consisting of E13/M48-259.69-P2 (amplification primers SEQ ID Nos: 1 and 2, mobility 259-260 bp), E16/M48-377.36-P2 (amplification primers SEQ ID Nos: 3 and 4, mobility 377-378 bp), E13/M48-261.30-P2 (amplification primers SEQ ID Nos: 5 and 6, mobility 261-262 bp) and E26/M62-076.8-P2 (amplification primers SEQ ID NOs: 7 and 8, mobility 76-77 bp), and wherein said plant is resistant to CVYV.

According to the present invention the terms "CVYV-resistant" and "CVYV resistance" relate to the ability of a plant to restrict the growth and development of the virus under normal pathogen pressure when compared to non-resistant, i.e. susceptible plants under similar environmental conditions and pest pressure.

The discrimination between resistant and susceptible plants can, for example, be determined by a method based on mechanical inoculation. To this end, a CVYV inoculum mixture was prepared by grinding 10 gram of fresh CVYV infected cucumber (*C. sativus* L.) leaves in a phosphate buffer ($KH_2PO_4$ pH=7.0). Subsequently, active charcoal and carborundum powder was added to the mixture. Melon seedlings were dusted with carborundum before inoculation.

The term "QTL" is used herein in its art-recognized meaning. The term "CVYV resistance conferring QTL" refers to a region located on a particular chromosome of melon that is associated with at least one gene that encodes for CVYV-resistance or at least a regulatory region, i.e., a region of a chromosome that controls the expression of one or more genes involved in CVYV-resistance.

A QTL may for instance comprise one or more genes of which the products confer the genetic resistance. Alternatively, a QTL may for instance comprise regulatory genes or sequences of which the products influence the expression of genes on other loci in the genome of the plant thereby conferring the CVYV-resistance.

According to the present invention, the term "molecular marker" refers to an indicator that is used in methods for visualizing differences in characteristics of nucleic acid sequences. Examples of such indicators are restriction fragment length polymorphism (RFLP) markers, amplified fragment length polymorphism (AFLP) markers, single nucleotide polymorphisms (SNPs), insertion mutations, microsatellite markers, sequence-characterized amplified regions (SCARs), cleaved amplified polymorphic sequence (CAPS) markers or isozyme markers or combinations of the markers described herein which defines a specific genetic and chromosomal location.

A "molecular marker linked to a QTL" as defined herein may thus refer to SNPs, insertion mutations as well as more usual AFLP markers or any other type of marker used in the field.

A preferred way to detect the present Cucumber Vein Yellowing Virus (CVYV)-resistance conferring Quantitative Trait Locus (QTL), or a CVYV-resistance conferring part thereof using the present molecular marker is Amplified fragment length polymorphism (AFLP). AFLP is a Polymerase Chain Reaction (PCR) based genetic fingerprinting technique that was developed in the early 1990's by Keygene N. V., Wageningen, The Netherlands.

In the AFLP method, restriction enzymes are used to cut genomic DNA, followed by ligation of complementary double stranded adaptors to the ends of the restriction fragments. A subset of the restriction fragments are then amplified using primer pairs complementary to the adaptor and restriction site fragments. The fragments are visualized, and the mobility or fragment size is determined relative to a standard DNA ladder to estimate its molecular weight in base pairs (bp). This can, for example, be done on denaturing polyacrylamide gels either through autoradiographic or fluorescence methodologies (Vos et al. Nucleic Acids Res. 1995 23(21): 4407).

The above AFLP method generally results in a multitude of nucleic acid amplification fragments of different sizes. By comparing the nucleic acid amplification fragments obtained from, for example, susceptible and resistant plants, discriminating nucleic acid amplification fragments, indicating the presence of, and segregating with, a specific Quantitative Trait Locus, can be identified. Such identified, and discriminating, amplification fragments are generally designated as markers of a particular phenotype, such as a resistant phenotype.

The present inventors have surprisingly found that plants comprising in their genome markers E13/M48-259.69-P2 (amplification primers SEQ ID Nos: 1 and 2, mobility 259-260 bp), E16/M48-377.36-P2 (amplification primers SEQ ID Nos: 3 and 4, mobility 377-378 bp), E13/M48-261.30-P2 (amplification primers SEQ ID Nos: 5 and 6, mobility 261-

262 bp) and E26/M62-076.8-P2 (amplification primers SEQ ID NOs: 7 and 8, mobility 76-77 bp) all had a Cucumber Vein Yellowing Virus (CVYV)-resistance phenotype, while plants lacking these markers, has a Cucumber Vein Yellowing Virus (CVYV)-susceptible phenotype. Therefore, the present markers are genetically linked to, and capable of, identifying, the present CVYV resistance conferring genetic element.

According to a preferred embodiment of the present invention, the markers, linked to the present resistance conferring Quantitative Trait Locus are selected to the group consisting of E16/M48-377.36-P2 ((amplification primers SEQ ID Nos: 3 and 4, mobility 377-378 bp), E13/M48-261.30-P2 (amplification primers SEQ ID Nos: 5 and 6, mobility 261-262 bp) and E26/M62-076.8-P2 (amplification primers SEQ ID NOs: 7 and 8, mobility 76-77 bp).

More preferably, the marker, linked to the present resistance conferring Quantitative Trait Locus, is E13/M48-261.30-P2 (amplification primers SEQ ID Nos: 5 and 6, mobility 261-262 bp).

According to a particularly preferred embodiment, the CVYV-resistance conferring QTL, or part thereof, is derived from melon landrace Cuc6491 (accession number NCIMB 41582).

The term melon accession Cuc6491 is used to indicate the source of the CVYV-resistance conferring QTL identified herein, and includes the accession as available from any of the public collections or depository Institutions well know to the skilled artisan, as well as CVYV-resistant derivatives thereof.

Subsequently, said resistance has been introduced into plants of the species *Cucumis melo*. According to the invention it has been found that it was possible to provide fully resistant plants wherein the present resistance trait, identified in Cuc6491 (accession number NCIMB 41582) has been stably fixed in the genome of the *C. melo* plant without the occurrence of necrotic symptoms. Once inoculated with CVYV, *C. melo* plants which contain the appropriate Cuc6491 (accession number NCIMB 41582) segment lack the typical CVYV mosaic symptoms in contrast to susceptible control plants.

The present invention thus also relates to a plant of the species *Cucumis melo*, said plant comprising a genetic element, for example an introgression fragment, comprising a CVYV-resistance-conferring QTL or a CVYV-resistance-conferring part thereof, which plant is resistant to CVYV. In a particular embodiment, the CVYV-resistant plant of the invention is not melon accession Cuc6491 (accession number NCIMB 41582).

The term melon accession Cuc6491 (accession number NCIMB 41582) is used to indicate the source of the CVYV-resistance conferring QTL identified herein, and includes the accession as available from any of the public collections or depository institutions well know to the skilled artisan, as well as CVYV-resistant derivatives thereof.

The present invention further relates to plant parts derived from a CVYV-resistant plant of the species *Cucumis melo* as described above. The plant part may be any part of a melon plant, including single cells and cell tissues such as plant cells that are intact in plants, cell clumps and tissue cultures from which melon plants can be regenerated. Examples of plant parts include, but are not limited to, single cells and tissues from pollen, ovules, leaves, embryos, roots, root tips, anthers, flowers, fruits, stems shoots, and seeds; as well as pollen, ovules, leaves, embryos, roots, root tips, anthers, flowers, fruits, stems, shoots, scions, rootstocks, seeds, protoplasts, calli, and the like. Preferably, the plant part is a seed or a fruit.

The present invention furthermore relates to a method for obtaining a CVYV resistant plant of the species *Cucumis melo*, comprising introducing a genetic element comprising a Cucumber Vein Yellowing Virus (CVYV)-resistance conferring Quantitative Trait Locus (QTL), or a CVYV-resistance conferring part thereof, genetically linked to at least one molecular marker, wherein said marker is selected from to the group consisting of E13/M48-259.69-P2 (amplification primers SEQ ID Nos: 1 and 2, mobility 259-260 bp), E16/M48-377.36-P2 (amplification primers SEQ ID Nos: 3 and 4, mobility 377-378 bp), E13/M48-261.30-P2 (amplification primers SEQ ID Nos: 5 and 6, mobility 261-262 bp) and E26/M62-076.8-P2 (amplification primers SEQ ID NOs: 7 and 8, mobility 76-77 bp), into the genome of said plant.

According to the present method, the marker is preferably selected from the group consisting of E16/M48-377.36-P2 (amplification primers SEQ ID Nos: 3 and 4, mobility 377-378 bp), and E13/M48-261.30-P2 (amplification primers SEQ ID Nos: 5 and 6, mobility 261-262 bp), and more preferably, the marker is E13/M48-261.30-P2 (amplification primers SEQ ID Nos: 5 and 6, mobility 261-262 bp).

According to a particularly preferred embodiment, the CVYV-resistance conferring QTL, or part thereof, is derived from melon Cuc6491 with accession number NCIMB 41582.

According to yet another preferred embodiment of the present method, the plant is not melon Cuc6491 with accession number NCIMB 41582

According to the present invention, a genetic element, i.e. a nucleic acid (preferably DNA) comprising the QTL of the present invention or a CVYV-resistance conferring part thereof, is used for the production of a CVYV-resistant melon plant. Thus, the invention provides for the use of a QTL of the present invention, or parts thereof, for producing a CVYV-resistant melon plant, which use involves the introduction of a nucleic acid sequence comprising said QTL in a CVYV-susceptible recipient melon plant. Said nucleic acid sequence may be derived from a suitable CVYV-resistant donor melon plant.

Preferably, the genetic element (nucleic acid fragment) comprising said CVYV-resistance conferring QTL, or part thereof, is derived from melon accession Cuc6491 (accession number NCIMB 41582). Other related melon plants that exhibit resistance to CVYV and comprise one or more genes that encode for CVYV resistance may also be utilized as CVYV-resistance donor plants as the present invention describes how this material may be identified.

The introduction of the genetic element, i.e., an (isolated) nucleic acid comprising the QTL of the invention, or a resistance-conferring part thereof, into a melon plant may be performed by any method known to the skilled person. Preferably the introduction is performed by crossing. In such an embodiment, a method of the present invention may comprise the step of crossing a plant of melon accession Cuc6491, or a CVYV-resistant derivative thereof, with a CVYV-susceptible melon plant; harvesting seed from the cross, growing said seed to produce Fl progeny plants; selfing or backcrossing said Fl progeny plants with the donor or recipient parent to produce F2 seeds; growing said F2 seeds to produce F2 progeny plants; determining the presence in the genome of at least one of said F2 progeny plants of a CVYV-resistance-conferring QTL, wherein the presence of said QTL is confirmed by detecting the presence in the DNA of said at least one F2 progeny plants of a marker linked to said QTL.

Said genetic element may furthermore be introduced by transformation, by protoplast fusion, by a doubled haploid technique or by embryo rescue or by any other nucleic acid transfer system, optionally followed by selection of offspring plants comprising the QTL and exhibiting CVYV-resistance. For transgenic methods of transfer, a nucleic acid sequence comprising a QTL for CVYV-resistance according to the present invention, or a CVYV-resistance-conferring part thereof, may be isolated from a donor plant by using methods known in the art and the thus isolated nucleic acid sequence may be transferred to the recipient plant by transgenic methods, for instance by means of a vector, in a gamete, or in any other suitable transfer element, such as a ballistic particle coated with said nucleic acid sequence.

Plant transformation generally involves the construction of an expression vector that will function in plant cells. In the present invention, such a vector comprises a nucleic acid sequence that comprises a QTL for CVYV-resistance of the present invention, or a CVYV-resistance-conferring part thereof, which vector may comprise a CVYV-resistance-conferring gene that is under control of or operatively linked to a regulatory element, such as a promoter. The expression vector may contain one or more such operably linked gene/regulatory element combinations, provided that at least one of the genes contained in the combinations encodes for CVYV-resistance. The vector(s) may be in the form of a plasmid, and can be used, alone or in combination with other plasmids, in a method for producing transgenic plants that are resistant to CVYV, using transformation methods known in the art, such as the *Agrobacterium* transformation system.

According to the present invention, the terms "introducing" or "introgressing" thus refer to both a natural and artificial process whereby genes, or nucleic acids of one species, variety or cultivar are transferred into the genome of another species, variety or cultivar, such as e.g. by crossing those species. The process may optionally be completed by backcrossing to the recurrent parent.

The present invention further relates to a CVYV-resistant plant of the species *Cucumis melo*, obtainable by a method as described above, as well as to any plant parts derived from said plant, such as, but not limited to, seeds and/or fruits. Said CVYV-resistant melon plant, or part thereof, thus comprises within its genome a QTL associated with CVYV-resistance, or a CVYV-resistance-conferring part thereof, as defined herein above, derived from melon accession Cuc6491 (accession number NCIMB 41582), or a CVYV-resistant derivative thereof, wherein said QTL or said CVYV-resistance conferring part thereof is not in its natural genetic background. Such a plant may be obtained by using various methods well known in the art, either transgenic or non-transgenic.

The present invention is further illustrated in the following Examples that are not intended to limit the scope of the invention in any way.

EXAMPLES

Example 1

QTL Mapping for CVYV Resistance in Melon
Introduction
A F2 population of 300 individuals was constructed from a cross between a CVYV susceptible Galia line ML100_PI and a CVYV resistant line Cuc6491 (accession number NCIMB 41582). All 300 plants were phenotyped at two plant development stages for their CVYV resistance level. Subsequently, markers were identified linked to QTLs that control the resistance to CVYV, using a QTL mapping approach.
Materials and Methods
Leaf material of 300 F2 individuals of the ML100× Cuc6491 (accession number NCIMB 41582) population as well as leaf material from both parental lines was obtained.

The phenotypic data used for QTL analysis consist of the level of resistance per F2 plant. The phenotype was measured on two days (May and June 2007) on one site. Two phenotypic classes were distinguished:

R=resistant

S=susceptible

Results

Forty-eight AFLP primer combinations (PCs) from a EcoRI/MseI matrix were screened on both parental lines ML 100 and Cuc6491 (accession number NCIMB 41582). The number of markers per PC is presented in Table 1.

TABLE 1

The number of markers scored and mapped per PC in the ML100 × Cuc6491 (accession number NCIMB 41582) genetic map

| PC KG | Markers scored | Markers mapped |
|---|---|---|
| E11/M48 | 18 | 18 |
| E11/M58 | 11 | 11 |
| E11/M60 | 15 | 14 |
| E14/M49 | 5 | 5 |
| E14/M51 | 3 | 3 |
| E14/M55 | 6 | 3 |
| E23/M47 | 16 | 15 |
| E23/M48 | 13 | 13 |
| E23/M50 | 14 | 14 |
| E23/M54 | 17 | 17 |
| E23/M55 | 5 | 5 |
| E23/M58 | 14 | 12 |
| E26/M59 | 8 | 5 |
| E26/M60 | 14 | 12 |
| E26/M62 | 9 | 7 |
| E14/M48 | 12 | 11 |
| E11/M49 | 18 | 17 |
| E14/M61 | 12 | 12 |
| Total | 210 | 194 |

The screening resulted in a data set containing 179 co-dominantly scored AFLP markers. A genetic map was constructed with the use of specialized software (CarteBlanche, Keygene N. V., Wageningen, The Netherlands).

A total of 154 out of the 179 co-dominantly scored markers were split into 15 linkage groups containing at least 3 markers with a total map length of 505.7 cM.

Windows QTL cartographer 2.0. Wang S., C. J. Basten and Z. B. Zeng; Department of Statistics North Carolina State University, USA) was used in order to identify QTLs. The analysis was performed by use of several statistical methods (Single Marker analysis, Interval Mapping and Composite Interval Mapping).

Single Marker Analysis (SMA) scans for correlations between the individual genotypes at marker positions and the corresponding phenotypical values. For each marker position a likelihood test is performed. A QTL is found when a peak exceeds the threshold value that has been declared. For the SMA, a threshold of LOD 3.5 was chosen.

Interval Mapping (IM) is an extension of the SMA method. The IM method uses two observable flanking markers to construct an interval in which a hypothetical QTL is placed and the likelihood tests are performed to either confirm or dismiss the QTL. LOD values are calculated for each incrementing step in the interval. Also the LOD score profile is calculated for the entire genome. IM calculates parameters such as the additive and dominant effects, the explained variance and a number of other parameters for the position being tested. When a peak exceeds a threshold value calculated by performing a permutation test the identification of a QTL is declared.

Composite Interval Mapping (CIM) performs the same analysis as the IM method, but takes into account the variance from other QTLs by including partial regression coefficients from markers in other regions of the genome. In theory, CIM gives more power and precision than Phenotypes Measured in May 2007

One QTL was detected. Associations between marker scores and phenotypes were detected when IM and CIM were used. A permutation test was performed to calculate the LOD significance thresholds for phenotypic data (IM: threshold LOD=3.91 and CIM: threshold LOD=3.97). The best marker, E26/M62-076.8 explains 19.2% of the variance with a LOD value of 4.81 in this subset of the F2 population (CIM).

Phenotypes Measured in June 2007

One QTL was detected. Associations between marker scores and phenotypes were detected when IM and CIM were used. A permutation test was performed to calculate the LOD significance thresholds for phenotypic data (IM: threshold LOD=3.73 and CIM: threshold LOD=3.60). This analysis confirms the presence of a single locus involved in CVYV resistance at Linkage Group 9 by means of marker M1 which explains 10.9% of the variance with a LOD value of 3.82 in this subset of the F2 population (CIM).

Conclusion

179 AFLP markers were scored on 92 F2 individuals of the ML100 (CVYV susceptible)×Cuc6491 (accession number NCIMB 41582) (CVYV resistant) F2 population. A genetic map was constructed containing 154 AFLP markers consisting of 15 linkage groups with a total map length of 505.7 cM.

QTL mapping using phenotypic data resulted in the identification of one CVYV QTL. This QTL was mapped on linkage group 9. For the first phenotypic measurement of May 2007 the best marker is E26/M62-076.8 and explains 19.2% of the variance with a LOD value of 4.81. For the phenotypic measurement of June 2007, M1 is the best marker which explains 10.9% of the variance with a LOD value of 3.82.

Example 2

Continuation Mapping of CVYV-Resistance Loci in Melon

Introduction

A F2 population of 300 individuals was constructed from a cross between a CVYV susceptible Galia line ML100 and a CVYV resistant line Cuc6491 (accession number NCIMB 41582). All F2 plants were phenotyped at two plant development stages for CVYV resistance level. In Example 1, QTL mapping using 92 F2 plants and F2 phenotype data resulted in the identification of one locus on Linkage Group 9 of the ML100×Cuc6491 (accession number NCIMB 41582) genetic map, which is putatively involved in the control of CVYV resistance.

Subsequently, pathotests have been performed on F3 families of F2 plants. This was aimed at mapping additional loci and validating the putative locus that was identified in the previous project by extension of the ML100×Cuc6491 (accession number NCIMB 41582) genetic map and by using the new phenotype data.

Materials

The biological material of Example 1 was used for this project; Leaf material of 300 F2 individuals (box nrs: SM07 332, SMO7 333, SMO7 334 and SMO7 335) of the ML100×Cuc6491 (accession number NCIMB 41582) F2 population were used. Also leaf material was obtained from the parental lines ML100 and Cuc6491. Additionally, biological material of a germplasm panel that was phenotyped for CVYV resistance (box NMB07-49) was used in this example.

The phenotypic data was generated in 3 different phenotype trials. The pathotests were executed as follows;

1) The first test was executed on F2 plants, which were infected by natural infection. The phenotype was measured on two dates (May and June 2007). Two phenotypic classes were distinguished; R=resistant, and S=susceptible. The phenotypes of both dates were separately used for identification of CVYV-resistance loci by a QTL mapping analysis.
2) The second phenotype trial was executed on F3 families. Depending on the number of available seeds for each F3 family up to 20 F3 individuals per family were infected by natural infection with CVYV (CVYV_F3 nat). Each F3 plant was scored for the level of resistance in 2 classes, resistant and susceptible respectively.
3) The third test was also executed on F3 families. Depending on the number of available seeds for each F3 family up to 25 F3 individuals per family were infected with CVYV using a mechanical infection method (CVYV_F3 mec). Also in this test, each F3 plant was scored for the level of resistance in 2 classes, resistant and susceptible respectively.

Results

Extension of the ML100×Cuc6491 (Accession Number NCIMB 41582) Genetic Map Focusing on the Top of LG 9

In Example 1, it was found that part of melon Linkage Group 9 was not covered by the ML100×Cuc6491 (accession number NCIMB 41582) genetic map. Furthermore, QTL mapping results suggest that a CVYV resistance locus is positioned in this region. In order to validate this, the ML100×Cuc6491 (accession number NCIMB 41582) genetic map was extended specifically for this region.

An additional AFLP screening by using a BSA approach (Michelmore et al. Proc. Natl. Acad. Sci. USA. (1991) 8(21): 9828) was executed to identify markers specifically for Linkage Group 9. This screening revealed Markers M2 and M3.

Subsequently, the two PCs that contain these markers were screened on the ML100×Cuc6491 (accession number NCIMB 41582) F2 individuals that were used for QTL mapping. Besides the two markers of special interest 26 additional markers were scored bringing the total data set on the 92 F2 plants to 210 codominantly scored markers.

A new ML100×Cuc6491 (accession number NCIMB 41582) genetic map was constructed according to the method described above. In this upgrade of the ML100×Cuc6491 (accession number NCIMB 41582) genetic map, a total of 195 out of the 231 co-dominantly scored markers were split into 15 Linkage Groups containing at least 3 markers with a total map length of 698.2 cM. The number of Linkage Groups (15) does still not correspond with the chromosome number of melon (n=12) suggesting that the genome is still not completely covered by the upgraded version of the ML100×Cuc6491 genetic map.

Also the size of the current map indicates that a part of the melon genome is not covered by this map. The size of melon maps is usually 1000-1500 cM. However, most important for this project is the extension of Linkage Group 9 of the ML100×Cuc6491 (accession number NCIMB 41582) genetic map by 29 cM through the positioning of markers M2 position on the 0 cM and M3 on 13.4 cM position.

After extending the ML100×Cuc6491 (accession number NCIMB 41582) genetic map, new QTL mapping analyses were executed in order to test the hypothesis of the map positions of the CVYV-resistance locus in a part of the particular chromosome that was not covered by the previous version ML100×Cuc6491 (accession number NCIMB 41582) genetic map. Also new phenotypic data on F3 families was included in these QTL analyses.

QTL Mapping

Windows QTL cartographer software 1 was used in order to identify CVYV-resistance loci. The analyses were performed by use of several statistical methods (Single Marker Analysis, Interval Mapping and Composite Interval Mapping).

QTL mapping was executed using the phenotype data of F3 families which were infected by natural infection (CVYV_F3 nat) and using the phenotype data of F3 families after mechanical infection (CVYV_F3 mec). The average phenotype value per F3 family for each infection method was used as input file for QTL analyses.

Mapping CVYV-resistance Loci with F2-Plants Natural CVYV Infection.

The results using the F2 phenotypes (Example 1) are briefly summarized: QTL mapping using the F2 phenotypes of the first date, May 2007, resulted in the identification of a putative CVYV resistance locus on the terminal part of Linkage Group 9 of the ML100×Cuc6491 (accession number NCIMB 41582) genetic map. The best marker is E26/M62-076.8 on 0 cM of the ML100×Cuc6491 (accession number NCIMB 41582) genetic map and explains 19.2% of the variance with a LOD value of 4.81. The same CVYV-resistance locus was identified using the F2 phenotypes of the second date. No other CVYV resistance loci were identified using the F2 phenotype data.

Mapping CVYV-resistance Locus with F3-Plants Natural CVYV Infection

QTL mapping using the F3 phenotypes after natural infection and using the upgraded version of the ML100×Cuc6491 genetic map resulted in the confirmation of the putative CVYV-resistance locus on the terminal part of Linkage Group 9 of the ML100×Cuc6491 (accession number NCIMB 41582) genetic map. The best marker is E26/M62-076.8 on position 29.1 cM of the updated version of the ML100×Cuc 6491 genetic map explains 39.9% of the variance with a LOD value of 3.8. (note that the cM position refers to the upgraded version of the ML100× Cuc6491 (accession number NCIMB 41582) genetic map which is constructed in this example). From the QTL LOD plot it can be concluded that the CVYV resistance on chromosome 9 is covered by the current genetic map.

Mapping CVYV-resistance Locus with F3-Plants Mechanical CVYV Infection

QTL mapping using the F3 phenotypes after mechanical infection resulted in a further confirmation of the CVYV-resistance locus on the terminal part of Linkage Group 9 of the ML100×Cuc6491 (accession number NCIMB 41582) genetic map.

Using the F3 phenotypes after mechanical infection, the best marker is M3 on 13.4 cM of the updated version of the ML100×Cuc6491 (accession number NCIMB 41582) genetic map and explains 54.1% of the variance with a LOD value of 9.7 using Interval Mapping.

It can be concluded that the CVYV-resistance gene is positioned between 13 and 37 cM of the upgraded version of the ML100×Cuc6491 genetic map.

Fine Mapping CVYV-resistance Locus

A BSA was executed in order to identify additional markers linked to the CVYV-resistance locus on Linkage Group 9. Forty eight PCs from the EcoRI/MseI +0/+A matrix were screened on a bulk of 10 plants with a extremely high average F3 phenotype value for both natural and mechanical infection methods and a bulk of 10 plants with a extremely low average F3 phenotype value for both natural and mechanical infection. This BSA resulted in the identification of 15 candidate linked markers.

Subsequently, four PCs containing the best candidate markers were validated on a panel of 48 F2 plants which are recombinant in the CVYV resistance region of Linkage Group 9. A total of five markers could be positioned on Linkage Group 9, of which only two markers map within the CVYV resistance region between 13.4 and 37 cM.

Validation of AFLP Markers Linked to CVYV-resistance on Linkage Group 9

Two PCs containing four AFLP markers linked to the CVYV resistance locus were screened on a germplasm panel that was partially phenotyped for CVYV resistance. Marker E26/M62-076.8 has the best predictive value. This marker scores the Cuc6491 (accession number NCIMB 41582) (=resistant) genotype "+" for 7 out of 8 resistant plants and it scores the ML100 (=susceptible) genotype "−" for all susceptible lines and all not phenotyped lines (which are expected to be susceptible). The predictive value of the other markers is poor.

Conclusion

A major QTL for CVYV-resistance from source Cuc6491 (accession number NCIMB 41582) was identified between 13.4 and 37 cM on Linkage Group 9 of the ML100 (=CVYV susceptible)×Cuc6491 (accession number NCIMB 41582) genetic map. Four markers from this region were validated on a germplasm panel. Marker E26/M62-076.8 has the best predictive value.

Example 3

The region between 13.4 and 37 cM on Linkage Group 9 of the ML100 (=CVYV susceptible)×Cuc6491 (accession number NCIMB 41582) genetic map was further fine mapped using a marker set between 15.8 cM and 63.6 cM. The results of this fine mapping are shown in table 2.

TABLE 2

Fine mapping of a region between 15.8 and 63.6 cM on Linkage Group 9.

|  | CVYV phenotype | E13/ M48- 259.69- P2 | E16/ M48- 377.36- P2 | E13/ M48- 261.30- P2 | E26/ M62- 076.8- P2 |
|---|---|---|---|---|---|
| R1 | R | + | + | + | + |
| R2 | R | + | + | + | + |
| R3 | R | + | + | + | + |
| R4 | R | + | + | + | + |
| Cuc 6491 | R | + | + | + | + |
| Cuc 6498 | R | + | + | + | + |
| Cuc 8632 | R | + | + | + | − |
| ML 0261 (339.495) | S | − | − | − | − |
| ML 0269 (339.524) | S | − | − | − | − |
| ML 0318 (339.517) | S | − | − | − | − |
| ML 2003 (340.460) | S | − | − | − | − |
| ML 2004 (330.968) | S | − | − | − | − |
| ML 2005 (330.969) | S | − | − | − | − |
| ML 2006 (330.970) | S | − | − | − | − |
| ML 2031 (339.480) | S | − | − | − | − |
| ML 2020 (339.445) | S | − | − | − | − |
| ML 2027 (339.477) | S | − | − | − | − |
| ML 2038 (339.395) | S | − | − | − | − |
| ML 2039 (339.437) | S | − | − | − | − |
| ML 2042 (339.443) | S | − | − | − | − |
| ML 2043 (339478) | S | − | − | − | − |
| ML 2064-5 | S | − | − | − | − |
| ML 2064-11 | S | − | − | − | − |
| ML 2066B | S | − | − | − | − |

TABLE 2-continued

Fine mapping of a region between 15.8 and 63.6 cM on Linkage Group 9.

|  | CVYV phenotype | E13/ M48- 259.69- P2 | E16/ M48- 377.36- P2 | E13/ M48- 261.30- P2 | E26/ M62- 076.8- P2 |
|---|---|---|---|---|---|
| ML 2067-1 | S | − | − | − | − |
| ML 2067-2 | S | − | − | − | − |
| ML 2067-7 | S | − | − | − | − |
| ML 2067-8 | S | − | − | − | − |
| S0610031-01 | S | − | − | − | − |
| S0610032-04 | S | − | − | − | − |
| S0610034-04 | S | − | − | − | − |
| S0610039-02 | S | − | − | − | − |
| S0610040-14 | S | − | − | − | − |
| S0610041-11 | S | − | − | − | − |
| S0610043-02 | S | − | − | − | − |
| S0610047-04 | S | − | − | − | − |
| S0610055-12 | S | − | − | − | − |
| S0610061-08 | S | − | − | − | − |
| S0610172-13 | S | − | − | − | − |
| S0610173-12 | S | − | − | − | − |
| S0610177-01 | S | − | − | − | − |
| S0610179-05 | S | − | − | − | − |
| S0513072-3 | S | − | − | − | − |
| S0513071-13 | S | − | − | − | − |
| S0611322-36 | S | − | − | − | − |
| S05210540-06 | S | − | − | − | − |
| S0513001-26 | S | − | − | − | − |
| S0513021-14 | S | − | − | − | − |
| S0612398-10 | S | − | − | − | − |
| S0622061-11 | S | − | − | − | − |
| S0622146-12 | S | − | − | − | − |
| S0622147-04 | S | − | − | − | − |
| S0622192-13 | S | − | − | − | − |
| S0622352-11 | S | − | − | − | − |
| S0622353-02 | S | − | − | − | − |
| S0622482-08 | S | − | − | − | − |
| S0622116-19 | S | − | − | − | − |
| S0622128-18 | S | − | − | − | − |
| PI | S | − | − | − | − |
| T | S | − | − | − | − |
| S | S | − | − | − | − |
| C | S | − | − | − | − |
| S0501002 | R | + | + | + | + |

As can be seen in Table 2, markers E13/M48-259.69-P2 (amplification primers SEQ ID Nos: 1 and 2, mobility 259-260 bp) and E26/M62-076.8-P2 (amplification primers SEQ ID NOs: 7 and 8, mobility 76-77 bp) correlated with 7 out of 8 resistant plants respectively whereas markers E16/M48-377.36-P2 (amplification primers SEQ ID Nos: 3 and 4, mobility 377-378 bp) and E13/M48-261.30-P2 (amplification primers SEQ ID Nos: 5 and 6, mobility 261-262 bp) showed a 100% correlation with the resistant phenotype.

Markers E13/M48-259.69-P2 (amplification primers SEQ ID Nos: 1 and 2, mobility 259-260 bp), E16/M48-377.36-P2 (amplification primers SEQ ID Nos: 3 and 4, mobility 377-378 bp), E13/M48-261.30-P2 (amplification primers SEQ ID Nos: 5 and 6, mobility 261-262 bp) and E26/M62-076.8-P2 (amplification primers SEQ ID NOs: 7 and 8, mobility 76-77 bp) mapped on positions 32.6, 32.7, 33.4 and 58.5 cM respectively. These markers are associated with the CVYV resistance locus with LOD scores of 9.9, 8.4, 9.9 and 4.5 respectively. The sequences of the above mentioned markers are presented in Table 3:

TABLE 3

Primer sequences of markers E13/M48-259.69-P2, E16/M48-377.36-P2, E13/M48-261.30- and E26/M62-076.8-P2

| Marker | Primer 1 | Primer 2 | Mobility (≈ length in base pairs) |
|---|---|---|---|
| E13/M48-259.69-P2 | GAC TGC GTA CCA ATT CAG (SEQ ID No: 1) | GAT GAG TCC TGA GTA ACA C (SEQ ID No: 2) | 259.69 |
| E16/M48-377.36-2P | GAC TGC GTA CCA ATT CCC (SEQ ID No: 3) | GAT GAG TCC TGA GTA ACA C (SEQ ID No: 4) | 377.36 |
| E13/M48-261.30-2P | GAC TGC GTA CCA ATT CAG (SEQ ID No: 5) | GAT GAG TCC TGA GTA ACA C (SEQ ID No: 6) | 261.30 |
| E26/M62-076.8-P | GAC TGC GTA CCA ATT CTT (SEQ ID No: 7) | GAT GAG TCC TGA GTA ACT T (SEQ ID No: 8) | 76.8 |

---

The invention claimed is:

1. A method for obtaining a CVYV resistant plant of the species *Cucumis melo*, comprising introducing a genetic element comprising a Cucumber Vein Yellowing Virus (CVYV)-resistance conferring Quantitative Trait Locus (QTL) genetically linked to at least one molecular marker, wherein said marker is selected from to the group consisting of E13/M48-259.69-P2 (amplification primers SEQ ID Nos: 1 and 2, mobility 259-260 bp), E16/M48-377.36-P2 (amplification primers SEQ ID Nos: 3 and 4, mobility 377-378 bp), E13/M48-261.30-P2 (amplification primers SEQ ID Nos: 5 and 6, mobility 261-262 bp) and E26/M62-076.8-P2 (amplification primers SEQ ID NOs: 7 and 8, mobility 76-77 bp), into the genome of said plant.

2. The method according to claim 1, wherein said marker is selected from the group consisting of E16/M48-377.36-P2 (amplification primers SEQ ID Nos: 3 and 4, mobility 377-378 bp), and E13/M48-261.30-P2 (amplification primers SEQ ID Nos: 5 and 6, mobility 261-262 bp).

3. The method according to claim 1, wherein said marker is E13/M48-261.30-P2 (amplification primers SEQ ID Nos: 5 and 6, mobility 261-262 bp).

4. The method according to claim 1, wherein said CVYV-resistance conferring QTL, or part thereof, is derived from melon Cuc6491 with accession number NCIMB 41582.

5. The method according to claim 1, wherein said plant is not melon Cuc6491 with accession number NCIMB 41582.

6. An isolated transgenic Cucumber Vein Yellowing Virus (CVYV)-resistant plant of the species *Cucumis melo*, obtained by a method according to claim 1.

7. A plant part from a plant according to claim 6, the plant part comprising said genetic element comprising a CVYV-resistance conferring QTL.

8. The plant part according to claim 7, wherein the plant part is a seed or a fruit.

* * * * *

UNITED STATES PATENT AND TRADEMARK OFFICE
CERTIFICATE OF CORRECTION

Page 1 of 1

PATENT NO. : 8,962,931 B2
APPLICATION NO. : 13/056631
DATED : February 24, 2015
INVENTOR(S) : Wietsche Kassies et al.

It is certified that error appears in the above-identified patent and that said Letters Patent is hereby corrected as shown below:

Title page, Column 1, Item (75) Inventors, Line 3, delete "Aguadulee" and insert -- Aguadulce --

Title page, Column 2, PUBLICATIONS, Line 3, delete "Cucurbi" and insert -- Cucurbit --

Title page, Column 2, Item (74) Attorney, Agent, or Firm, Line 1, delete "Film" and insert -- Firm --

In the Claims

Column 14, Line 66, Claim 1, delete "from to" and insert -- from --

Column 15, Line 5, Claim 1, delete "NOs:" and insert -- Nos: --

Signed and Sealed this
Ninth Day of June, 2015

Michelle K. Lee
*Director of the United States Patent and Trademark Office*

SEQUENCE LISTING

<160> NUMBER OF SEQ ID NOS: 8

<210> SEQ ID NO 1
<211> LENGTH: 18
<212> TYPE: DNA
<213> ORGANISM: Artificial Sequence
<220> FEATURE:
<223> OTHER INFORMATION: primer 1 marker E13/M48-259.69-P2

<400> SEQUENCE: 1
gactgcgtac caattcag                 18

<210> SEQ ID NO 2
<211> LENGTH: 19
<212> TYPE: DNA
<213> ORGANISM: Artificial Sequence
<220> FEATURE:
<223> OTHER INFORMATION: primer 2 marker E13/M48-259.69-P2

<400> SEQUENCE: 2

```
gatgagtcct gagtaacac                                              19

<210> SEQ ID NO 3
<211> LENGTH: 18
<212> TYPE: DNA
<213> ORGANISM: Artificial Sequence
<220> FEATURE:
<223> OTHER INFORMATION: primer 1 marker E16/M48-377.36-P2

<400> SEQUENCE: 3
gactgcgtac caattccc                                               18

<210> SEQ ID NO 4
<211> LENGTH: 19
<212> TYPE: DNA
<213> ORGANISM: Artificial Sequence
<220> FEATURE:
<223> OTHER INFORMATION: primer 2 marker E16/M48-377.36-P2

<400> SEQUENCE: 4
gatgagtcct gagtaacac                                              19

<210> SEQ ID NO 5
<211> LENGTH: 18
<212> TYPE: DNA
<213> ORGANISM: Artificial Sequence
<220> FEATURE:
<223> OTHER INFORMATION: primer 1 marker E13/M48-261.30-P2

<400> SEQUENCE: 5
gactgcgtac caattcag                                               18

<210> SEQ ID NO 6
<211> LENGTH: 19
<212> TYPE: DNA
<213> ORGANISM: Artificial Sequence
<220> FEATURE:
<223> OTHER INFORMATION: primer 2 marker E13/M48-261.30-P2

<400> SEQUENCE: 6
gatgagtcct gagtaacac                                              19

<210> SEQ ID NO 7
<211> LENGTH: 18
<212> TYPE: DNA
<213> ORGANISM: Artificial Sequence
<220> FEATURE:
<223> OTHER INFORMATION: primer 1 marker E26/M62-076.8-P

<400> SEQUENCE: 7
gactgcgtac caattctt                                               18

<210> SEQ ID NO 8
<211> LENGTH: 19
<212> TYPE: DNA
<213> ORGANISM: Artificial Sequence
<220> FEATURE:
<223> OTHER INFORMATION: primer 2 marker E26/M62-076.8-P

<400> SEQUENCE: 8
gatgagtcct gagtaactt                                              19
```